United States Patent [19]

Landscheidt et al.

[11] Patent Number: 5,648,570

[45] Date of Patent: Jul. 15, 1997

[54] PROCESS FOR PREPARING SUBSTITUTED CHLOROAROMATICS

[75] Inventors: Heinz Landscheidt, Duisburg; Witold Broda, Neunkirchen-Seelscheid; Alexander Klausener, Köln, all of Germany

[73] Assignee: Bayer Aktiengesellschaft, Leverkusen, Germany

[21] Appl. No.: 667,533

[22] Filed: Jun. 21, 1996

[30] Foreign Application Priority Data

Jun. 29, 1995 [DE] Germany ............... 195 23 641.6

[51] Int. Cl.⁶ ........................................... C07C 22/00
[52] U.S. Cl. .................................................. 570/201
[58] Field of Search ...................................... 570/201

[56] References Cited

U.S. PATENT DOCUMENTS

| | | |
|---|---|---|
| 4,622,431 | 11/1986 | Briody et al. ............... 570/201 |
| 4,714,785 | 12/1987 | Manner ......................... 570/201 |
| 4,730,046 | 3/1988 | Leone-Bay et al. .......... 570/201 |

FOREIGN PATENT DOCUMENTS

| | | |
|---|---|---|
| 0223421A2 | 5/1987 | European Pat. Off. . |
| 0514683A1 | 11/1992 | European Pat. Off. . |

OTHER PUBLICATIONS

H.J. Bestmann, Lieb, Ann. Chem., vol. 698, pp. 106–108 (1966).

J. Baddiley, J. Chem. Soc., pp. 678–679 (1944).

A., Albert et al, J. Chem. Soc., pp. 1666–1679 (1964).

J.D. Park et al, J. Org. Chem., vol. 27, pp. 1462–1463 (1962).

A. Surrey et al. J. Ann. Chem. Soc., vol. 76, pp. 1109–1113 (1954).

*Primary Examiner*—Alan Siegel
*Attorney, Agent, or Firm*—Sprung Horn Kramer & Woods

[57] ABSTRACT

Substituted chloroaromatics are obtained in a simple manner in virtually isomer-free form when substituted phenols of the formula (II)

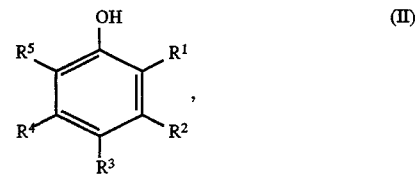

where $R^1$ to $R^5$ are each, independently of one another, hydrogen, $C_1$–$C_{10}$-alkyl, unsubstituted or substituted $C_6$–$C_{10}$-aryl or halogen, with at least one of these radicals being different from hydrogen, are reacted with dichlorotriphenylphosphorus.

12 Claims, No Drawings

PROCESS FOR PREPARING SUBSTITUTED CHLOROAROMATICS

The present invention relates to a process for preparing substituted chloroaromatics by reacting substituted phenols with dichlorotriphenylphosphorus.

Chloroaromatics having a wide variety of substitution patterns are required for a wide variety of applications, for example as precursors for the preparation of crop protection agents and pharmaceuticals (see Ullmann, Encyclopädie der technischen Chemie, 4th Edition, page 499 ff.).

Fundamentally, substituted chloroaromatics can be prepared by direct chlorination of substituted aromatic hydrocarbons. However, this always results in formation of undesired isomers, so that either a low product quality has to be accepted or isomerically pure compounds can only be obtained after carrying out complicated separation operations.

A further process for preparing chloroaromatics comprises the nitration of aromatics, subsequent reduction of the nitro compound, diazotization of the amine obtained and decomposition of the diazonium salt thus formed in the presence of copper chloride. Here too, undesired isomers are formed in the first step. In addition, such a multistage synthesis sequence is of no interest from an economic point of view owing to the large outlay in terms of chemicals and working capacity.

Methods described predominantly in the area of heterocyclic compounds allow selective replacement of a hydroxyl group by a chlorine substituent. Thus, Org. Synth. Coll. Vol. 3, p. 272 describes the reaction of 4-hydroxyquinoline with phosphorus oxychloride, J. Am. Chem. Soc. 76, 1109 (1954) describes the reaction of 4,10-dihydroxy-1,7-phenanthroline with phosphorus pentachloride and J. Org. Chem. 27, 1462 (1962) describes the reaction of a hydroxypyrimidine derivative with phosphorus oxychloride. According to J. Chem. Soc. 1964, 1666, chloropteridines can be obtained by reaction of corresponding hydroxy compounds with phosphorus pentachloride and, according to J. Chem. Soc. 1944, 678, chloropyrimidines can be obtained from the corresponding hydroxy compounds and phosphorus oxychloride. The processes mentioned are restricted to the conversion of specific heterocycles. They can obviously be transferred neither to other heterocycles, nor to carbocyclic systems. In addition, the processes mentioned give not only the desired chloroheterocycles but also the reaction products of the inorganic phosphorus compounds used in a non-regenerable form, so that in the case of industrial utilization expensive disposal of these phosphorus compounds is required.

Lieb. Ann. Chem. 698, 106 (1966) describes the decomposition of a chloroformic ester obtained from phenol with triphenylphosphine, with chlorobenzene being obtained as reaction product. In this process, the chloroformic ester has to be prepared in a complicated manner. In addition, it is not clear whether substituted phenols can also be converted into substituted chloroaromatics by this process.

There is therefore a need for a process which makes it possible to prepare substituted chloroaromatics in a simple manner from readily available starting materials.

A process has now been found for preparing substituted chloroaromatics of the formula (I)

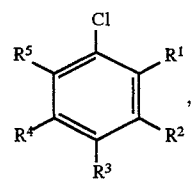

where
R$^1$ to R$^5$ are each, independently of one another, hydrogen, C$_1$–C$_{10}$-alkyl, unsubstituted or substituted C$_6$–C$_{10}$-aryl or halogen, with at least one of these radicals being different from hydrogen, which is characterized in that substituted phenols of the formula (II)

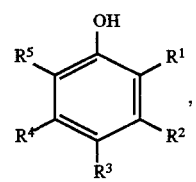

where
R$^1$ to R$^5$ are as defined for formula (I),
are reacted with dichlorotriphenylphosphorus.

Insofar as R$^1$ to R$^5$ represent C$_1$–C$_{10}$-alkyl, preference is given to straight-chain or branched C$_1$–C$_6$-alkyl, in particular C$_1$–C$_4$-alkyl. Particular preference is given to methyl.

Insofar as R$^1$ to R$^5$ represent unsubstituted or substituted C$_6$–C$_{10}$-aryl, preference is given to phenyl and naphthyl, with suitable substituents being, for example, C$_1$–C$_4$-alkyl and halogen. Particular preference is given to unsubstituted or substituted phenyl, with suitable substituents being, in particular, methyl, fluorine and chlorine. Very particular preference is given to phenyl.

Insofar as R$^1$ to R$^5$ represent halogen, they can be, for example, fluorine, chlorine or bromine. Preference is given to fluorine and chlorine, in particular chlorine.

Particularly preferred individual compounds of the formula (II) are monochlorophenol, monochlorocresol, dichlorophenols and dichlorocresols. Corresponding, particularly preference is given to preparing dichlorobenzenes, dichlorotoluenes, trichlorobenzenes and trichlorotoluenes according to the invention.

Chlorine-containing compounds of the formula (II) can not only be used in pure form, but also in the form of reaction mixtures as are obtained, for example, in the chlorination of those phenols of the formula (II) in which at least 2 and at most 4 of the radicals R$^1$ to R$^5$ represent hydrogen.

A particularly advantageous process for preparing substituted chloroaromatics of the formula (I) in which at least one of the radicals R$^1$ to R$^5$ represents chlorine is therefore characterized in that a phenol of the formula (II) in which at least 2 and at most 4 of the radicals R$^1$ to R$^5$ represent hydrogen is first chlorinated in a customary manner, e.g. using chlorine in the presence of a solvent, and the reaction mixture obtained is then reacted with dichlorotriphenylphosphorus.

Dichlorotriphenylphosphorus can be used as such in the process of the invention. However, preference is given to generating the dichlorotriphenylphosphorus in situ. In situ generation can be carried out, for example, by reacting triphenylphosphine with chlorine or triphenylphosphine oxide with phosgene in an inert solvent (see, for example, Z. Anorg. Chem. 250, 257 (1943) and Gazz. Chim. Ital. 77, 509

(1947)) and using the reaction mixture obtainable in this way in the process of the invention. It is surprising that dichlorotriphenylphosphorus prepared in situ can be used without significant impairment of the course of the reaction in respect of reaction rate and selectivity.

The process of the invention is preferably carried out in the presence of an inert solvent. Suitable solvents are, for example, halogenoaromatics such as chlorobenzene, dichlorobenzenes and trichlorobenzenes. Inert solvents can be employed, for example, in amounts of from 0.1 to 100 l per mol of dichlorotriphenylphosphorus used. If the dichlorotriphenylphosphorus is prepared in situ, all or part of the inert solvent can be used in this in situ preparation.

The process of the invention can, for example, be carried out by adding the substance to be chlorinated of the general formula (II) to dichlorotriphenylphosphorus, for example in a molar ratio of from 0.5 to 10, preferably from 0.8 to 5, based on the dichlorotriphenylphosphorus initially charged. The compound of the formula (II) can, for example, be added as such, in the case of chlorine-containing compounds if desired as described above as a reaction mixture from the chlorination, or mixed with an inert solvent, e.g. of the type described above. The reactants can be combined, for example, at temperatures in the range from 0° to 200° C.

The reaction of the invention can, for example, be carried out at temperatures in the range from 50° to 250° C. The reaction is complete when the evolution of hydrogen chloride gas ceases.

After the reaction is complete, the reaction mixture then present can, for example, be worked up by first distilling off the inert solvent at atmospheric pressure or reduced pressure and then distilling off the product of the formula (I). The product of the formula (I) thus separated off can, if desired, be further purified by further downstream steps, for example by distillation, crystallization and other methods known per se to those skilled in the art.

The residue remaining after separating off the solvent and the product of the formula (I) consists predominantly of triphenylphosphine oxide which can be reconverted into dichlorotriphenylphosphorus. For example, the residue can be taken up in an inert solvent, e.g. of the abovementioned type, and be reconverted into dichlorotriphenylphosphorus by the action of phosgene. Dichlorotriphenylphosphorus thus obtained can be reused for reactions with a compound of the formula (I).

The process of the invention has a series of advantages. Thus, it allows the preparation of substituted chloroaromatics from readily available starting materials in a process which can be carried out in a simple manner, with the substituted chloroaromatics being obtained in good yields. An important aspect is that the process enables the preparation of virtually isomerically pure substituted chloroaromatics as are demanded for further processing into, for example, crop protection agents and pharmaceuticals.

EXAMPLES

EXAMPLE 1

Over a period of 3 hours, 239 g of chlorine were passed into a mixture of 880 g of triphenylphosphine and 1000 ml of chlorobenzene while stirring vigorously, with the temperature being 40° C. for the first 2 hours, then 50° C. A solution of 456 g of 2-chloro-3-methyl-phenol in 200 ml of chlorobenzene was allowed to run dropwise into the mixture obtained above at 40° C. over the course of 90 minutes. At atmospheric pressure, the temperature of the reaction mixture was subsequently gradually increased to 150° C., with vigorous evolution of gaseous hydrogen chloride commencing when 80° C. was reached. During the reaction and subsequent thereto, a total of 1314 g of hydrogen chloride-containing chlorobenzene was collected as distillate until a bottom temperature of 150° C. was reached. The residue was subjected to a distillation at from 5 to 10 mbar. This gave 2,3-dichlorotoluene in a yield of 92% of theory.

EXAMPLE 2 a) Preparation of 2,4-dichloro-6-methyl-phenol (reaction mixture)

Over a period of 2 hours, 142 g of chlorine were passed into a solution of 108 g of o-cresol in 500 ml of chlorobenzene while cooling in ice.

b) Preparation of 2,3,5-trichlorotoluene

Over a period of 2 hours, 70 g of chlorine were passed into a mixture of 250 g of triphenylphosphine and 250 ml of chlorobenzene while stirring vigorously, with the temperature being 40° C. The solution thus obtained was then reacted with the solution obtained as described in a) by allowing the latter solution to run in dropwise at 40° C. over a period of 60 minutes. The temperature of the reaction mixture was gradually increased to 200° C., with hydrogen chloride-containing chlorobenzene distilling off. After cessation of the gas evolution, a pressure of 20 mbar was applied and distillation was continued. The distillate thus obtained was subjected to a further fractional distillation. This gave 106 g of 2,3,5-trichlorotoluene.

What is claimed is:

1. A process for preparing a substituted chloroaromatic of the general formula (I)

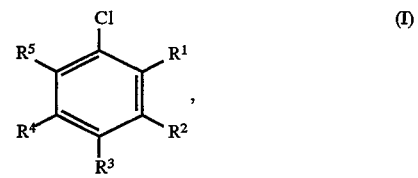

where
R¹ to R⁵ are each, independently of one another, hydrogen, $C_1$–$C_{10}$-alkyl, unsubstituted or substituted $C_6$–$C_{10}$-aryl or halogen, with at least one of these radicals being different from hydrogen,
in which a substituted phenol of the formula (II)

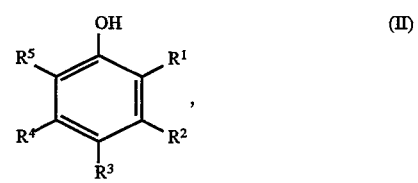

where
R¹ to R⁵ are as defined for formula (I),
is reacted with dichlorotriphenylphosphorus.

2. The process of claim 1, in which in the formulae (I) and (II) R¹ to R⁵ are each, independently of one another, hydrogen, straight-chain or branched $C_1$–$C_4$-alkyl, unsubstituted naphthyl or phenyl or $C_1$–$C_4$-alkyl- and/or halogen-substituted naphthyl or phenyl, fluorine or chlorine, with at least one of these radicals being different from hydrogen.

3. The process of claim 1, in which chlorine-containing compound of the formula (II) is used in the form of a chlorination reaction mixture.

4. The process of claim 1 for preparing a substituted chloroaromatic of the formula (I) in which at least one of the radicals $R^1$ to $R^5$ represents chlorine, in which process a phenol of the formula (II) in which at least 2 and at most 4 of the radicals $R^1$ to $R^5$ represent hydrogen is first chlorinated in a customary manner and the reaction mixture obtained is then reacted with dichlorotriphenylphosphorus.

5. The process of claim 1, in which the dichlorotriphenylphosphorus is generated in situ by reacting triphenylphosphine with chlorine in an inert solvent.

6. The process of claim 1, in which the dichlorotriphenylphosphorus is generated in situ by reacting triphenylphosphine oxide with chlorine in an inert solvent.

7. The process of claim 1, which is carried out in the presence of an inert solvent.

8. The process of claim 1, in which the substance of the general formula (II) to be chlorinated is added to dichlorotriphenylphosphorus in a molar ratio of from 0.5 to 10.

9. The process of claim 1, in which the reactants are combined at from 0° to 200° C. and the reaction is carried out at temperatures in the range from 50° to 250° C.

10. The process of claim 1, in which the reaction mixture present after the reaction is complete is worked up by distilling off the product of the formula (I).

11. The process of claim 1, in which the reaction mixture present after the reaction is complete is worked up by distilling off the product of the formula (I) and the inert solvent.

12. The process of claim 1, which is carried out in the presence of an inert solvent and after separating off the solvent and the product of the formula (I) the residue is dissolved in an inert solvent, dichlorotriphenylphosphorus is again generated therefrom by the action of phosgene and dichlorotriphenylphosphorus thus obtained is reused for the reaction with a compound of the formula (I).

\* \* \* \* \*